(12) United States Patent
Choi (10) Patent No.: US 10,722,886 B2
(45) Date of Patent: Jul. 28, 2020

(54) APPARATUS FOR SEPARATING FINE PARTICLES AND SEPARATING METHOD USING SAME

(71) Applicant: UNIVERSITY-INDUSTRY COOPERATION GROUP OF KYUNG HEE UNIVERSITY, Yongin-si (KR)

(72) Inventor: Sungyoung Choi, Gyeonggi-do (KR)

(73) Assignee: CURIOSIS CO., LTD., Seoul (KR)

( * ) Notice: Subject to any disclaimer, the term of this patent is extended or adjusted under 35 U.S.C. 154(b) by 37 days.

(21) Appl. No.: 15/321,681

(22) PCT Filed: Jun. 22, 2015

(86) PCT No.: PCT/KR2015/006306
§ 371 (c)(1),
(2) Date: Dec. 22, 2016

(87) PCT Pub. No.: WO2015/199395
PCT Pub. Date: Dec. 30, 2015

(65) Prior Publication Data
US 2017/0203298 A1    Jul. 20, 2017

(30) Foreign Application Priority Data
Jun. 23, 2014    (KR) .......................... 10-2014-0076310

(51) Int. Cl.
*B01L 3/00*    (2006.01)
*C12M 1/24*    (2006.01)
(Continued)

(52) U.S. Cl.
CPC ....... *B01L 3/502761* (2013.01); *B01L 3/0217* (2013.01); *C12M 1/24* (2013.01);
(Continued)

(58) Field of Classification Search
CPC ..... B01L 2200/0652; B01L 2400/0487; B01L 2400/086; B01L 3/502753;
(Continued)

(56) References Cited

U.S. PATENT DOCUMENTS

| 5,595,712 A | * | 1/1997 | Harbster | ............... B01F 5/0604 422/129 |
| 2004/0166025 A1 | * | 8/2004 | Chan | ....................... B01F 5/061 422/400 |

(Continued)

FOREIGN PATENT DOCUMENTS

| JP | 2005-205387 A | 8/2005 |
| KR | 10-2010-0074874 A | 7/2010 |

(Continued)

OTHER PUBLICATIONS

International Search Report of PCT/KR2015/006306 dated Feb. 10, 2015. (w/English language translation from WIPO).

*Primary Examiner* — Dean Kwak
(74) *Attorney, Agent, or Firm* — Lex IP Meister, PLLC (57) ABSTRACT

Disclosed is an apparatus for separating microparticles and a method of separating the microparticles from a fluid containing the microparticles to separately provide the microparticles and the fluid from which the microparticles are removed using the same. The microparticles are capable of being separated even via a manual operation including a pipette or a syringe, regardless of a flow rate.

6 Claims, 9 Drawing Sheets

(51) Int. Cl.
*B01L 3/02* (2006.01)
*C12N 5/078* (2010.01)
*C12M 1/00* (2006.01)
*G01N 1/34* (2006.01)
*B01D 43/00* (2006.01)

(52) U.S. Cl.
CPC ............ *C12N 5/0641* (2013.01); *B01D 43/00* (2013.01); *B01L 2200/0652* (2013.01); *B01L 2400/0487* (2013.01); *B01L 2400/086* (2013.01); *C12M 47/04* (2013.01); *G01N 1/34* (2013.01)

(58) Field of Classification Search
CPC ..... B01L 2200/0636; B01L 2300/0816; B01L 2300/0864; B01L 3/0217; B01L 3/502746; B01L 3/502761

USPC .............. 422/73, 501–505, 514; 436/10, 180
See application file for complete search history.

(56) References Cited

U.S. PATENT DOCUMENTS

| | | | |
|---|---|---|---|
| 2006/0039829 A1* | 2/2006 | Suk .................. | B01L 3/502746 422/400 |
| 2007/0161051 A1 | 7/2007 | Tsinberg et al. | |
| 2011/0303586 A1* | 12/2011 | Sim .................. | B01L 3/502761 209/268 |
| 2013/0130226 A1 | 5/2013 | Lim et al. | |

FOREIGN PATENT DOCUMENTS

| | | |
|---|---|---|
| KR | 10-2013-0000396 A | 1/2013 |
| KR | 10-2014-0073051 A | 6/2014 |

* cited by examiner

APPARATUS FOR SEPARATING FINE PARTICLES AND SEPARATING METHOD USING SAME

TECHNICAL FIELD

The present invention relates to an apparatus for separating microparticles and a separation method using the same.

More particularly, the present invention relates to an apparatus for separating microparticles from a fluid containing the microparticles regardless of a flow rate, and a separation method using the same.

BACKGROUND ART

A process for separating and removing analysis-hindering cells, other than target molecules, is required in order to precisely and rapidly perform molecular analysis of biosamples.

Cells and cell suspensions are separated using a centrifuge in the related art, but there are drawbacks in that (1) high-priced apparatuses are required to perform pre-treatment and (2) it is difficult to transport the apparatuses.

A current particle separation method using microfluid dynamics may be broadly classified into an active separation method and a passive separation method.

In the active separation method, particles are separated using an external energy field such as an electric field. Representative examples thereof may include capillary electrophoresis and dielectrophoresis separation methods.

Capillary electrophoresis is frequently used to separate materials having polarity, such as proteins or DNA, according to size, but has drawbacks in that a high voltage is required during separation and in that non-polar particles such as cells cannot be separated.

On the other hand, a difference in the dielectrophoretic performance of particles exposed to a non-uniform electric field, depending on the size and the kind of the particles, is used in the dielectrophoresis separation method. Accordingly, there is a merit in that non-polar molecules or cells are capable of being separated without a pre-treatment process. However, the dielectrophoresis separation method may cause electrolysis in an electrolyte solution such as a cell medium, and accordingly has a problem in that a cytophilic solution cannot be used as a separation solution. Further, in the case of a biological sample such as a cell, the applied voltage may affect the activity of the cell, thus limiting the use of the resultant separated material for the purpose of cell therapy.

Unlike the active separation method, the passive separation method has a merit in that microparticles are separated without an additional apparatus other than a microflow channel by using flow energy for sample supply.

Therefore, recently, various microfluid systems adopting the aforementioned merit have been actively studied. Examples thereof include a separation method using a difference in position of particles, which are arrayed depending on the size of the particles in a microchannel (Japanese Registered Patent No. 2005-205387).

However, the passive separation method has a problem in that the microflow rate must be precisely controlled between a sample flow and a sheath flow in order to array the particles at the same initial position in the microflow channel before the particles are separated.

Further, a cell separation element, such as an inertial fluidic element and a hydrophoretic element based on microfluidics has been developed, but the developed elements have a drawback in that efficiency depends greatly on the driving flow rate of the element.

Specifically, the hydrophoretic element has low cell removal efficiency when the flow rate is increased, and the inertial fluidic element has low cell removal efficiency when the flow rate is reduced.

Therefore, there is a problem in that a special high-priced syringe pump having high flow-rate precision is required in order to drive the hydrophoretic element or the inertial fluidic element.

Further, additional electric or physical energy is required in order to manipulate biological microparticles such as cells and DNA. In order to use additional energy, a separate energy source apparatus must be provided to a microfluidic element, and accordingly, a complicated manufacturing process is inevitable.

Therefore, since the manufacturing process and the operation mechanism of the microfluidic element are complicated, there is a limit in the extent to which the portability and the practicality of the element can be increased.

Accordingly, there is a demand for a highly portable and practical apparatus for separating microparticles from a fluid containing the microparticles regardless of a flow rate, and for a separation method using the same.

DISCLOSURE

Technical Problem

The present invention is to provide an apparatus for separating microparticles using the internal structural characteristics of a microfluid channel, regardless of a flow rate, and a method of separating the microparticles.

Technical Solution

In order to accomplish the above object, the present invention provides an apparatus for separating microparticles, the apparatus including a microfluid injection unit for injecting a fluid containing the microparticles;

a microparticle separation unit connected to the microfluid injection unit to separate the microparticles from the injected fluid;

a first discharge unit connected to the microparticle separation unit to discharge the separated microparticles; and a second discharge unit connected to the microparticle separation unit to discharge the fluid from which the microparticles are removed, wherein the microparticle separation unit includes a microfluid channel unit, the microfluid channel unit includes expanding channel units and reducing channel units that alternately repeat, a lateral surface of the microfluid channel unit is inclined at a predetermined angle based on the primary flow direction of the fluid, and the microparticle separation unit is driven using pressure generated by a pressure generator fastened to the microfluid injection unit.

The microfluid injection unit of the apparatus for separating the microparticles may include the pressure generator used to inject the microfluid, and the microparticle separation unit may be driven using the pressure generated by the pressure generator.

In an embodiment of the present invention, the pressure generator of the microfluid injection unit may be any one of a pipette or a syringe.

Further, the injected fluid may flow toward the microfluid channel due to the pressure generated by the pressure generator.

Here, "inclination" means the angle of a slope, and more precisely, a slope excluding 0°, 90°, and 180° degrees.

The inclined lateral surface of the microfluid channel of the present invention is neither vertical nor horizontal, and in the embodiment, the inclination angle of the inclined lateral surface may be greater than 00 and less than 180°, excluding 90°. In another embodiment, the inclination angle of the inclined lateral surface of the microfluid channel of the present invention may range from 300 to 150°, excluding 90°. In another embodiment, the inclination angle of the inclined lateral surface of the microfluid channel of the present invention may range from 60° to 120°, excluding 90°. In another embodiment, the inclination angle of the inclined lateral surface of the microfluid channel of the present invention may be 70° to 100°, excluding 90°.

Further, in the embodiment of the present invention, the width of the expanding channel unit may be at least twice as large as the width of the reducing channel unit. In the embodiment, the width of the expanding channel unit of the present invention may be two to ten times as large as that of the reducing channel unit.

In the embodiment of the present invention, the width of the reducing channel unit may be equal to or larger than the diameter of the microparticles to be separated, and may be up to four times as large as the diameter of the microparticles to be separated.

In the embodiment of the present invention, the height of the microfluid channel unit may be at least three times the width of the reducing channel unit. In the embodiment, the height of the microfluid channel unit of the present invention may be three to ten times the width of the reducing channel unit.

In the embodiment of the present invention, the expanding channel unit and the reducing channel unit may be 10 μm or more in length. In the embodiment, the length of each of the expanding channel unit and the reducing channel unit of the present invention may be 10 to 1000 μm.

In the embodiment of the present invention, the microfluid separation unit may include the two or more microfluid channel units, and the two or more microfluid channel units may be layered parallel to each other.

In the embodiment of the present invention, the microfluid separation unit may include the ten or more microfluid channel units, and the two or more microfluid channel units may be layered parallel to each other. In the embodiment, the 10 to 100 microfluid channel units of the present invention may be layered parallel to each other.

In the present invention, since a flow rate is proportional to a given pressure but is in inverse proportion to the resistance of the channel, the microfluid channel units that are layered parallel to each other may serve to increase the cell treatment amount under a given pressure.

In the embodiment of the present invention, the first discharge unit, through which the microparticles are discharged, may be positioned on the lateral surface of the channel to form a lateral-surface discharge unit. The second discharge unit, through which the fluid from which the microparticles are removed is discharged, may be positioned at the middle of the channel to form a middle discharge unit.

In the present invention, the size of the separated microparticles may be 5 to 50 μm.

In order to accomplish the above object, the present invention also provides a method of separating microparticles using an apparatus for separating the microparticles, the method including dividing a fluid containing the microparticles into the microparticles and the fluid from which the microparticles are removed.

The method of separating the microparticles comprising providing a fluid containing the microparticles using a pressure generator (step a);

fastening the pressure generator to the apparatus for separating the microparticles according to the present invention (step b);

driving the microparticle separation unit using a pressure generated by the pressure generator fastened to a microfluid injection unit, thus separating the microparticles (step d); and separately discharging the microparticles and the fluid from which the microparticles are removed (step e).

ADVANTAGEOUS EFFECTS

According to the present invention, microparticles can be separated from a fluid containing the microparticles using the internal structural characteristics of a microfluid channel, regardless of a flow rate.

According to the present invention, the microparticles can be simply and rapidly separated from the fluid containing the microparticles even in a limited environment without a high-priced apparatus for precisely controlling the flow rate.

According to the present invention, an apparatus for separating the microparticles can be driven even using a manual operation including a pipette or a syringe.

According to the present invention, cells can be effectively separated, removed, or concentrated from a cell suspension.

According to the present invention, blood corpuscles and plasma can be separated from the blood, and a cell medium including cells can be divided into the cells and the cell medium.

According to the present invention, a cell removal process, which must be performed for the purpose of molecular analysis of a cell suspension, can be embodied in a single chip to simplify and quicken pre-treatment of samples without a high-priced large apparatus such as a centrifuge, thereby stably and precisely performing molecular analysis.

DESCRIPTION OF DRAWINGS

FIG. 6 is a view showing an experiment for removing and separating cells using the apparatus for separating the microparticles according to the Example of the present invention, in which the uppermost part of FIG. 6(*a*) is a picture showing that a 1 ml pipette is fastened to the apparatus for separating the microparticles according to the Example of the present invention via a 1 ml pipette tip, the middle part of FIG. 6(*a*) is a picture showing the separation of corpuscle cells from a blood sample using the apparatus for separating the microparticles according to the Example of the present invention, the lowermost part of FIG. 6(*a*) is a sectional view showing the flow of the separated microparticles (red arrows) and the flow of the separated fluid (a black arrow), the left of FIG. 6(*b*) is a picture showing the blood sample before separation, the right of FIG. 6(*b*) is a picture showing the blood sample after separation, performed using the apparatus for separating the microparticles according to the Example of the present invention, and a scale bar is 100 μm.

FIG. 7(*a*) is a picture showing that a syringe is fastened to the apparatus for separating the microparticles according to the Example of the present invention, FIG. 7(*b*) is a sectional view showing a flow of the separated microparticles (green arrows) and a flow of the separated fluid (a white arrow) in the apparatus, and FIG. 7(*c*) shows the result (percentage) of the cytotoxicity experiments of the cells separated using the apparatus for separating the microparticles according to the Example of the present invention and a conventional centrifuge, in which a scale bar is 100 μm.

FIG. 8(*a*) shows fluorescent microscopic pictures showing the array of the microparticles using the apparatus for separating the microparticles of Example 1 of the present invention and Comparative Example 1, and FIG. 8(*b*) shows fluorescence profiles of the array.

DESCRIPTION OF THE REFERENCE NUMERALS IN THE DRAWINGS

- 101: Silicon wafer
- 102: Photoresist
- 103: Poly(dimethylsiloxane) (PDMS)
- 104: Biopsy punch
- 105: Discharge unit
- 106, 201: Fluid injection unit
- 202: Inclined wall structure of lateral surface of channel
- 203, 306, 605: First discharge unit (lateral-surface discharge unit)
- 204, 307, 606: Second discharge unit (middle discharge unit)
- 205, 403: Wall inclined at a predetermined angle and corresponding to lateral surface of channel
- 301: Fluid containing microparticles
- 302, 601: Pipette
- 303, 603: Pipette tip
- 206, 304: Microparticle separation unit
- 305: Pipette driving unit
- 401: Expanding channel unit
- 402: Reducing channel unit
- 404: Rotation flow
- 405: Microparticle
- 501, 502: Inlet part of microparticle separation unit
- 602: Blood sample
- 604: Apparatus for separating microparticles

MODE FOR INVENTION

Examples of the present invention will be described in greater detail below, with reference to the accompanying drawings. The following Examples are set forth to illustrate the present invention, but the scope of the present invention is not limited to the following Examples.

Preparation Example

Figure 1:
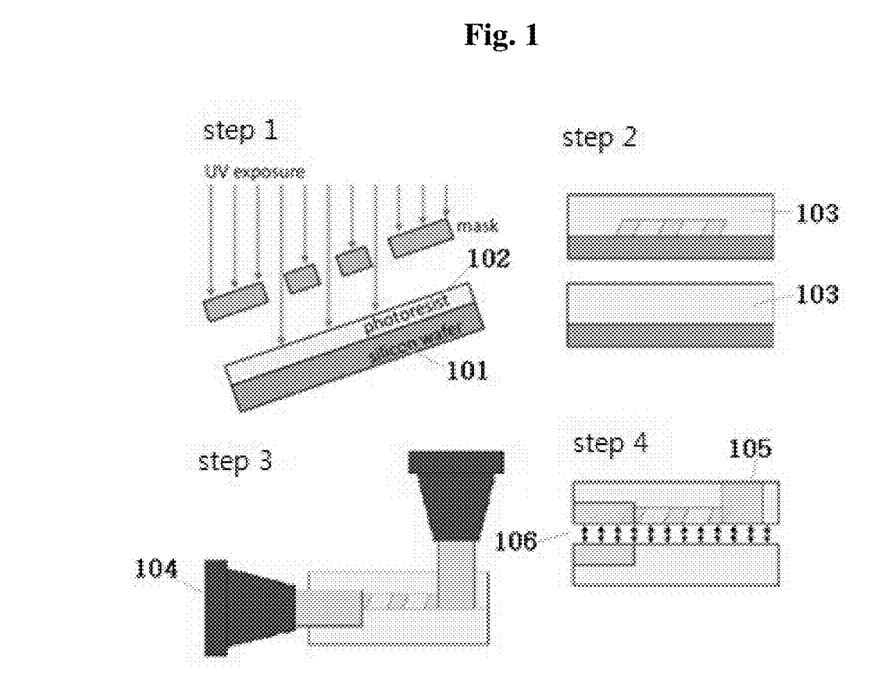
FIG. 1 shows a process of manufacturing an apparatus for separating microparticles according to an Example of the present invention.

FIG. 1 shows the manufacture of an apparatus for separating microparticles according to an Example of the present invention. A microparticle separation unit according to the present invention is manufactured according to a micromolding process using poly(dimethylsiloxane) (PDMS).

Referring to FIG. 1, first, the upper part of a silicon wafer 101 is spin-coated with a SU-8 photoresist (MicroChem Corp., Newton, Mass.) 102 to a predetermined thickness (for example, 60 to 70 μm), dried (baking), and obliquely exposed to UV rays so that the angle between the UV rays and a direction perpendicular to the silicon wafer 101 is 5°. Subsequently, the silicon wafer is baked and then developed to form a final photoresist pattern (mold) having an inclined structure (step 1). The length, the width, and the height of the photoresist, and the quantity of UV radiation may be controlled depending on the design and process conditions.

Subsequently, the silicon mold is duplicated to manufacture a microfluid apparatus using poly(dimethylsiloxane) (PDMS) 103 (step 2). Preferable examples of the polymer material used in the polymer substrate include polymethyl methacrylate (PMMA), polyacrylate, polycarbonate, polycyclic olefin, polyimide, or polyurethane, in addition to poly(dimethylsiloxane) (PDMS).

Specifically, a mixture (ratio of 10:1) (PDMS Sylgard184 kit, Dow Chem Corp., Midland, Mich.) including a prepolymer of PDMS and a curing agent is poured onto the mold, which has a photoresist pattern and which is manufactured for the purpose of channel duplication, and is cured at 70° C. for 1 hour. The duplicated PDMS channel unit is exposed to oxygen plasma for 40 sec and then attached to a glass slide. The structure of the PDMS channel unit corresponds to the structure of the channel unit of the microparticle separation unit of FIG. 2. Each channel unit includes expanding channel units and reducing channel units that alternately repeat. The width and length of the expanding channel unit are 60 μm and 40 μm, respectively, and the width and length of the reducing channel unit are 20 μm and 40 μm, respectively. The height of the channel is 72.5 μm. The microfluid channel unit has a structure including 160 expanding channel units and 160 reducing channel units repeatedly formed therein.

In order to form a discharge unit 105 and an injection unit 106 through a PDMS slab, holes for the discharge unit 105 and the injection unit 106 are formed using a 1.5 mm biopsy punch 104 (step 3).

The PDMS slabs having the holes therein are treated using oxygen plasma, arrayed, and irreversibly combined (step 4).

Poly(dimethylsiloxane) (PDMS), which is used to manufacture the separation apparatus of the present invention, imparts leak-proof interconnection performance when subjected to a predetermined pressure due to the deformability thereof.

Comparative Preparation Example

The apparatus is manufactured according to the same procedure as in the Preparation Example, except that a silicon wafer 101 is exposed to UV rays incident in a direction perpendicular to the surface of the silicon wafer and that the height of the channel is 62.9 µm.

<Example 1> Apparatus for Separating Microparticles

Figure 2:
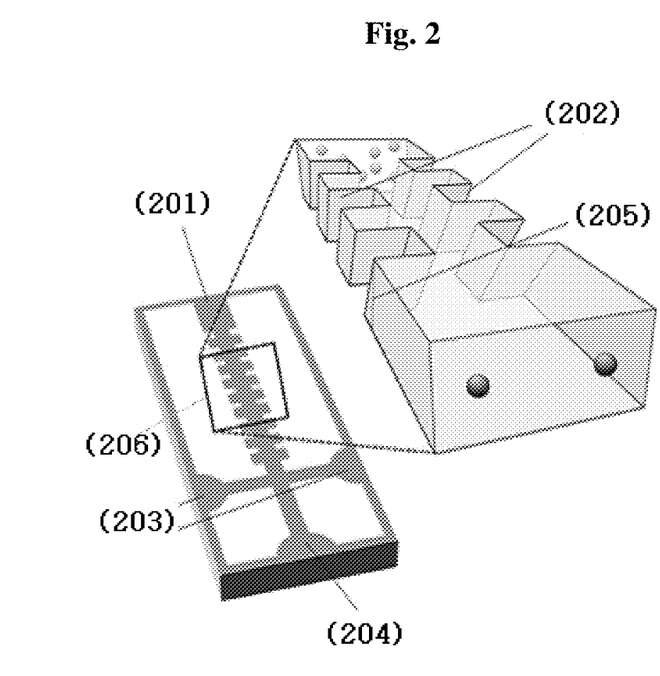
FIG. 2 is a perspective view of the apparatus for separating the microparticles according to the Example of the present invention.

FIG. 2 is a perspective view of an apparatus for separating microparticles according to the Example of the present invention.

Referring to FIG. 2, the apparatus for separating the microparticles includes a microfluid injection unit 201 for injecting a fluid containing the microparticles, a microparticle separation unit 206 connected to the microfluid injection unit to thus separate the microparticles from the injected fluid, a first discharge unit (lateral surface) 203 connected to the microparticle separation unit to thus discharge the separated microparticles, and a second discharge unit (middle) 204 connected to the microparticle separation unit to thus discharge the microfluid from which the microparticles are removed. The microparticle separation unit includes a microfluid channel unit 206, and the microfluid channel unit 206 includes expanding channel units and reducing channel units that alternately repeat.

Examples of the fluid containing the microparticles include blood, but are not limited thereto. Examples of the microparticles include blood corpuscles, cells, bacteria, viruses, and DNA, but are not limited thereto.

The lateral surface 202 of the microfluid channel unit has an inclined portion 205 inclined at a predetermined angle based on the primary flow direction of the fluid, and the inclination angle is neither 0° nor 90°. The primary flow direction of the fluid means the main flow direction of the microfluid flowing from an inlet part to an outlet part. That is, the inclination angle with respect to the primary flow direction of the fluid means the angle of inclination in a direction that is neither perpendicular nor parallel to the primary flow direction of the fluid. For example, the inclination angle may be more than 0° and less than 180°, but not 90°. For example, the inclination angle is 85°. Each channel unit includes expanding channel units and reducing channel units that alternately repeat. The width and length of the expanding channel unit are 60 µm and 40 µm, respectively, and the width and length of the reducing channel unit are 20 µm and 40 µm, respectively. The height of the channel is 72.5 µm.

In the apparatus for separating the microparticles, the microparticle separation unit is driven using the pressure generated by a pressure generator fastened to the microfluid injection unit.

The pressure generator fastened to the microfluid injection unit is a means for generating a predetermined pressure for injection of the microfluid. The pressure generator may be any one of a pipette, a syringe, a peristaltic pump, or a syringe pump, and the microfluid separation unit may be driven even by the pressure generated using a pipette or syringe, which is capable of being manually operated. The predetermined pressure may be, for example, 10 kPa to 608.4 kPa.

In the present invention, hydrophoretic equilibrium positions (Lp) may be explained using the following parameters.

$$L_p \propto f\left(\frac{w_c}{d}, \frac{h}{d}, Re\right) \quad (1)$$

In Equation (1), Wc is the width of the reducing channel, h is the height of the channel, and d is the diameter of the particle (microparticle) to be separated. Re is a Reynolds number defined by $\rho uL/\mu$ (Re=$\rho uL/\mu$). $\rho$ is the density of the fluid (liquid), u is the flow rate of the fluid (liquid), L is the characteristic dimension of the fluid channel, and p is the viscosity of the fluid (liquid). That is, Re is proportional to the flow rate of the fluid.

The width of the expanding channel unit may be at least twice as large as the width of the reducing channel unit.

The width of the reducing channel may be equal to or larger than the diameter of the microparticles to be separated, and may be up to four times as large as the diameter of the microparticles to be separated. This relationship may be represented by the following Equation (2).

$$d \leq Wc \leq 4d \quad (2)$$

The length of each of the expanded channel and the reduced channel may be 1 µm or more.

The height of the microfluid channel may be at least three times the width of the reducing channel unit.

<Comparative Example 1> Apparatus for Separating Microparticles

The apparatus for separating the microparticles of Comparative Example 1 has the same structure as that of Example 1, except that the lateral surface of the microfluid channel unit is inclined at an angle of 90° based on the primary flow direction of the fluid and that the height of the channel is 62.9 µm.

Figure 5:
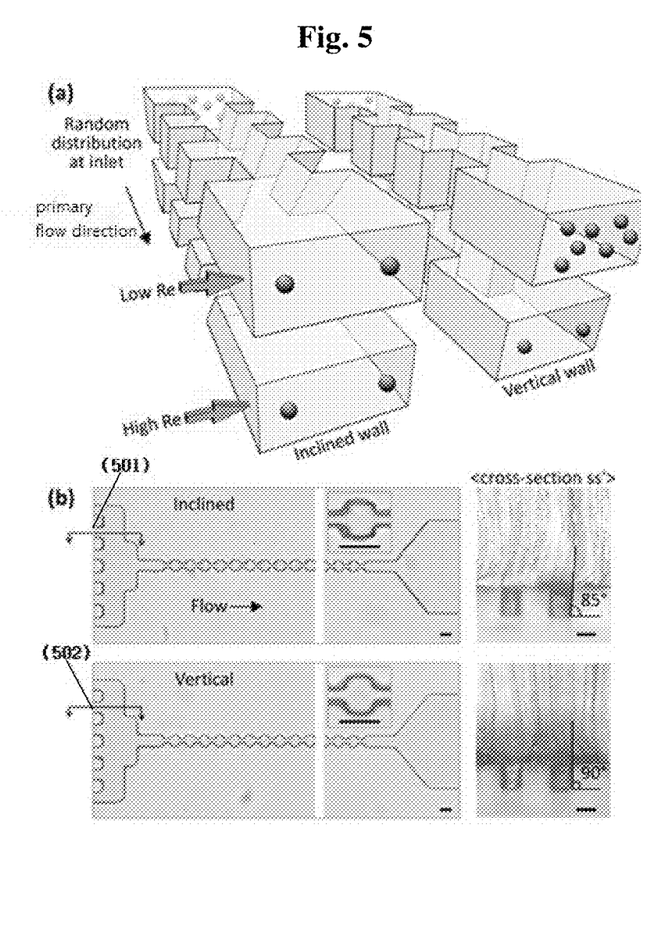
FIG. 5(a) is a perspective view showing the structure and schematic driving of the microparticle separation units according to the Example of the present invention and the Comparative Example.
FIG. 5(b) shows a plan view and a sectional view of the microfluid separation units according to the Example of the present invention and the Comparative Example, in which the left of FIG. 5(a) and the upper part of FIG. 5(b) show the microparticle separation unit of Example 1, the right of FIG. 5(a) and the lower part of FIG. 5(b) show the microparticle separation unit of Comparative Example 1, and a scale bar is 50 μm.

<Example 2> Apparatus for Separating Microparticles Including a Plurality of (Two or More) Microfluid Channel Units The apparatus for separating the microparticles is the same as that of Example 1, except that a microfluid separation unit includes two or more microfluid channel units and that two or more microfluid channel units are layered parallel to each other (see FIG. 5(a)).

For example, the apparatus of Example 2 may be the same as the apparatus for separating the microparticles of Example 1, except that the microfluid separation unit includes ten or more microfluid channel units and that the ten or more microfluid channel units are layered parallel to each other.

In the Example, the apparatus of Example 2 may be the same as the apparatus for separating the microparticles of Example 1, except that the microfluid separation unit includes ten microfluid channel units and that the ten microfluid channel units are layered parallel to each other.

<Example 3> Method of Separating Microparticles

Figure 3:
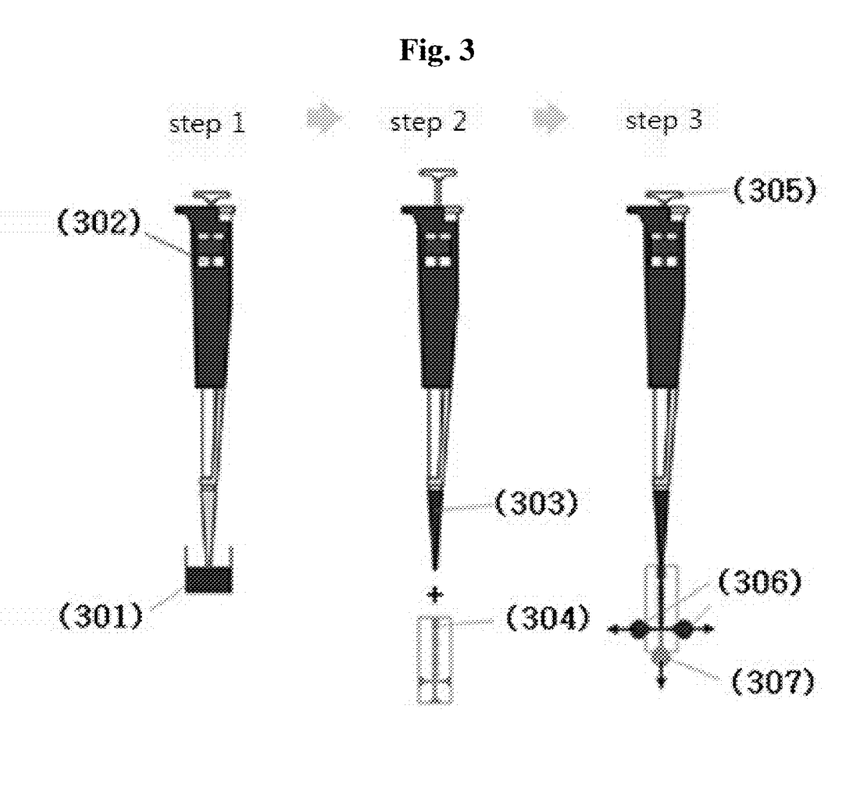
FIG. 3 shows a method of separating microparticles using the apparatus for separating the microparticles according to the Example of the present invention and a pipette.

FIG. 3 shows a method of separating microparticles using the apparatus for separating the microparticles according to the Example of the present invention and a pipette.

Referring to FIG. 3, the method of separating the microparticles includes providing a fluid 301 containing the microparticles using a pipette 302 as a pressure generator (step 1), fastening the pipette 302 to the apparatus for separating the microparticles according to Example 1 via a pipette tip 303 (step 2), and pressing a driving unit 305 of the pipette, which drives the apparatus for separating the microparticles to thus discharge the fluid 301 containing the microparticles from the pressure generator, thereby dividing the fluid 301 containing the microparticles into the microparticles and the fluid (step 3). The fluid 301 containing the microparticles discharged from the pressure generator is divided using the rotation flow of the microparticles shown in FIG. 4 during step 3.

Figure 4:
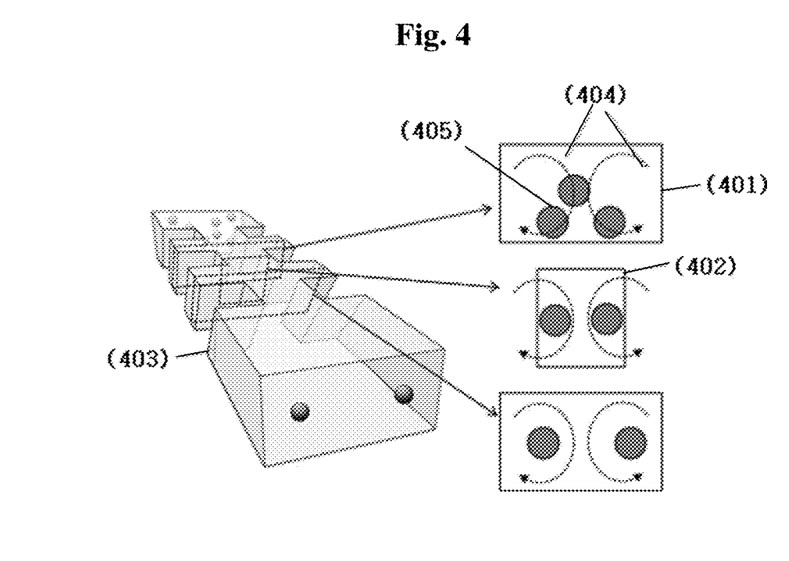
FIG. 4 shows a perspective view of a microparticle separation unit according to the Example of the present invention and a sectional view of a microfluid channel unit causing a rotation flow of the microparticles.

Referring to FIG. 4, a microfluid channel unit includes expanding channel units 401 and reducing channel units 402 that alternately repeat, the lateral surface of the microfluid channel unit has an inclined portion 403 inclined at a predetermined angle based on a primary flow direction of the fluid, and the inclination angle is neither 0° nor 90°. The primary flow direction of the fluid means the main flow direction of the microfluid flowing from an inlet part to an outlet part.

A secondary pressure gradient field may be formed in a direction perpendicular to the primary flow direction of the fluid due to the inclined structure of the lateral surface of the microfluid channel unit, thus causing a rotation flow 404 of the microparticles moving toward the lateral surface of the microfluid channel unit.

Accordingly, the microparticles 405 injected into the microfluid channel unit may move to the lateral surface of the microfluid channel unit due to the rotation flow.

Due to the reducing channel unit 402 causing the one-sided array of the microparticles, the microparticles moving to the lateral surface of the microfluid channel unit may be prevented from moving through the rotation flow 404 back to the middle of the microfluid channel unit.

Accordingly, the microparticles may be arrayed close to the lateral surface wall of the channel due to the rotation flow 404 and the reducing channel unit 402.

Meanwhile, when a flow rate (the rate of the fluid) is high, in addition to the rotation flow and the one-sided array of the microparticles, inertial force may affect the flow of the microparticles.

Referring to FIG. 4, the microparticles move via inertia to the middle of the wide side of the channel unit due to the inertial force in the rectangular channel having a predetermined section. Since the reducing channel unit 402 of the microparticle channel unit has a height that is greater than the width thereof (for example, the height is at least three times as large as the width), the microparticles are arrayed close to the lateral surface wall of the channel due to the inertial force.

Therefore, in the apparatus for separating the microparticles according to the present invention, the constant array position may be maintained even at a high flow rate, thereby constantly and stably arraying the microparticles regardless of the flow rate.

Specifically, referring to FIG. 5(a), in the apparatus for separating the microparticles according to the present invention (the apparatus for separating the microparticles of Example 1), when the lateral surface of the microfluid channel is inclined at a predetermined angle (left), the particles may move close to the lateral surface wall of the channel mainly due to hydrophoresis in a low Re region, and the particles may move toward two types of flows close to the longitudinal side of the channel mainly due to the inertial force in a high Re region. Accordingly, the particles may be arrayed regardless of the flow rate.

In contrast, in the apparatus for separating the microparticles of Comparative Example 1, when the lateral surface of the channel unit has a vertical wall (right), the particles may not move toward the lateral surface of the channel, but may be influenced by the flow rate in a low Re region.

Example 3-1. Method of Separating Corpuscles (Microparticles) from Blood (Fluid) Using a Pipette as a Pressure Generator The present example relates to a method of separating corpuscles (microparticles) from blood (fluid) using a pipette as a pressure generator.

Figure 6:
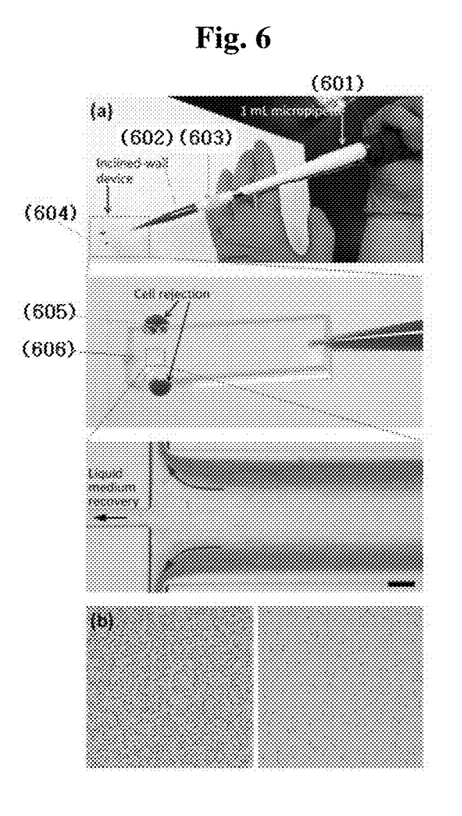

FIG. 6 is a view showing an experiment of removing and separating cells using the apparatus for separating the microparticles according to the Example of the present invention, in which the uppermost part of FIG. 6(a) is a picture showing that a 1 ml pipette is fastened to the apparatus for separating the microparticles according to the Example of the present invention via a 1 ml pipette tip, the middle part of FIG. 6(a) is a picture showing the separation of corpuscle cells from a blood sample using the apparatus for separating the microparticles according to the Example of the present invention, the lowermost part of FIG. 6(a) is a sectional view showing the flow of the separated microparticles (red arrows) and the flow of the separated fluid (black arrows), the left of FIG. 6(b) is a picture showing the blood sample before separation, the right of FIG. 6(b) is a picture showing the blood sample after separation is performed using the apparatus for separating the microparticles according to the Example of the present invention, and a scale bar is 100 μm.

Referring to FIG. 6(a), a method of separating the microparticles includes providing a blood sample 602, which is a fluid containing the microparticles (corpuscle cells or the like), using a pipette 601 as a pressure generator (step 1), fastening the pipette 601 to the apparatus 604 for separating the microparticles according to Example 1 via a pipette tip 603 (step 2), and pressing the driving unit of the pipette, which drives the apparatus for separating the microparticles to thus discharge the blood sample 602, that is, the fluid 301 containing the microparticles (corpuscle cells or the like), from the pressure generator, thereby dividing the blood sample 602, that is, the fluid 301 containing the microparticles (corpuscle cells or the like), into the microparticles (corpuscle cells or the like) and the fluid (a cell suspension from which the corpuscle cells are removed) (step 3).

Specifically, the blood sample was obtained from the Korean Red Cross in compliance with safety regulations. Before the blood sample was used, the blood sample was diluted using a Dulbecco's phosphate-buffered saline (DPBS) at a ratio of 1:10 so that the final concentration of red corpuscle cells (RBCs) was about $3.4 \times 10^8$ cell $mL^{-1}$.

After 1 mL of the diluted blood sample was sampled using the pipette 601, the pipette 601 was fastened to the apparatus 604 for separating the microfluids of the present invention via the 1 mL tip 603.

The driving unit of the micropipette was pressed until an initial resistance point to thus compress air in an air displacement micropipette (Gilson Inc., Middleton, Wis.), thereby generating the pressure under which the fluid started to flow in the apparatus.

With respect thereto, in the case where a single apparatus was used, an average volumetric flow rate (qav) was 29.3±3.3 μL $min^{-1}$ when calculated.

An average pressure (Pay) applied to the apparatus was about 90 kPa, and the average volumetric flow rate (qav) was multiplied by the hydraulic resistance of the apparatus, which was determined using a numerical simulation, whereby the pressure (Pay) was calculated.

As for the apparatus for separating the microfluid according to Example 2, including ten microfluid channel units that were layered parallel to each other, the average volumetric flow rate (qav) was improved at least seven-fold (29.3±3.3 μL min$^{-1}$) without a reduction in the operation efficiency of the apparatus.

The pressure was calculated by multiplying the flow rate and the hydraulic resistance together. The volume of the fluid per unit time was measured at an outlet part to calculate the flow rate, and the pressure obtained using the numerical simulation was divided by the flow rate to calculate the hydraulic resistance.

As shown in FIG. 6(b), when the blood sample was divided using the apparatus for separating the microfluid according to the present invention, the concentration of red corpuscle cells was significantly reduced in the blood sample after cell separation (right), compared to the case before the cells were separated (left).

From the above-described experiment, it can be seen that when the cells were separated using the apparatus for separating the microfluid according to the present invention, separation efficiency was very high, specifically 88.9±2.7% with respect to a treatment amount of 1.8×10$^5$ cell S$^{-1}$. The recovery ratio of the separated fluid was 20.0±1.7%.

The separation treatment amount of the cells means the number of injected cells per unit time. The separation efficiency was calculated by dividing the number of separated cells by the number of injected cells. The recovery ratio of the fluid was calculated by dividing the volume of the fluid obtained at the outlet part by the volume of the injected fluid.

Example 3-2. Method of Separating Cells (Microparticles) from a Culture Medium (Fluid) Using a Syringe as a Pressure Generator The present example relates to a method of separating cells (microparticles) from a culture medium (fluid) using a syringe as a pressure generator.

Figure 7:
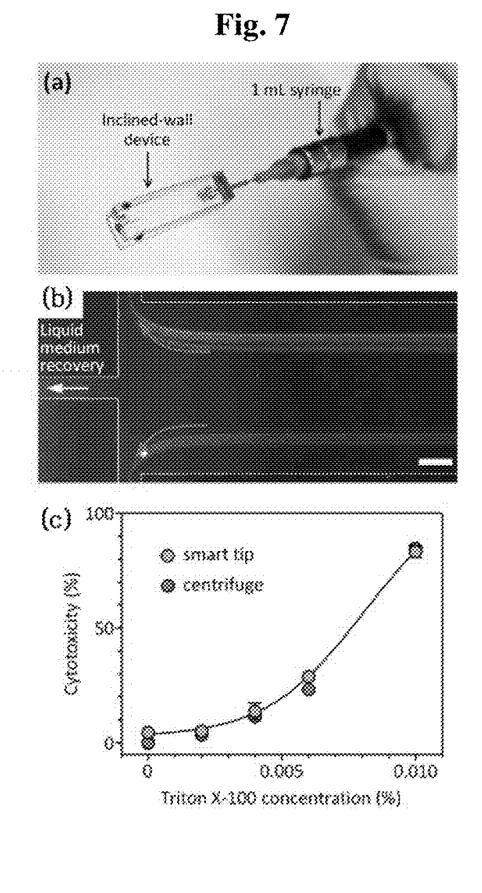

FIG. 7(a) is a picture showing that the syringe is fastened to the apparatus for separating the microparticles according to the Example of the present invention, FIG. 7(b) is a sectional view showing the flow of the separated microparticles (green arrows) and the flow of the separated fluid (a black arrow) in the apparatus, and FIG. 7(c) shows the result of cytotoxicity experiments on the cells separated using the apparatus for separating the microparticles according to the Example of the present invention and a conventional centrifuge, in which a scale bar is 100 μm. In this Example, the separation efficiency of the cells separated using the apparatus for separating the microfluid according to the present invention was very high, namely, 99.9%. The recovery ratio of the separated fluid was 18.7±0.9%.

<Experimental Example 1> Cytotoxicity Experiment

FIG. 7(c) shows the result (percentage) of cytotoxicity experiments performed on the cells separated using the apparatus for separating the microparticles according to the Example of the present invention and the conventional centrifuge, and the scale bar is 100 μm.

After the cell treated using Triton X-100 according to the Example of the present invention was separated using the apparatus for separating the microparticles, the apparatus fastened to the 1 mL syringe, and the conventional centrifuge, the cytotoxicity (%) was measured from the collected cell culture medium.

Specifically, a Jurkat cell was cultured in RPMI (WELGENE Inc., Korea) suspended using a 10% FBS (WELGENE) and a 1% antibiotic solution containing penicillin and streptomycin (WELGENE). In order to visualize the flow of the cell, the cell was washed with DPBS (WELGENE) and then dyed using a 10 μM CFDA cell tracer (Invitrogen) at room temperature for 15 min. After the dyeing, the cell was washed twice with DPBS.

The Jurkat cell was exposed to Triton X-100 at various concentrations (0 to 0.1%) in a $CO_2$ incubator for 30 min. Subsequently, the fluid from which the microparticles were separated was obtained using the apparatus for separating the microparticles, to which the syringe was fastened, according to the present invention (manual injection at room temperature for 3 min), and the centrifuge (at 1000 rpm and room temperature for 5 min). 50 micro-liters of the separated culture medium was used in lactate dehydrogenase (LDH) analysis. The lactate dehydrogenase (LDH) analysis was performed in accordance with the manufacturer's directions (#88953, Pierce, Rockford, Ill.), and the absorbance was then measured at 490 nm. The cytotoxicity percentage is the percentage value obtained by subtracting the LDH activity of the non-treated cell from the LDH activity of the cell treated using 0.1% Triton X-100. In the case of 0.1% Triton X-100, the toxicity was represented by 100%, and in the case of non-treatment, the toxicity was represented by 0%.

The $IC_{50}$ value of Triton X-100 determined from the reaction-capacity curve of FIG. 6(b) was 0.0076%. In the cytotoxicity analysis, there was no significant difference between the samples manufactured using the syringe fastened to the microseparation apparatus according to the present invention and the centrifuge (p=0.11, two-tailed paired t-test). It can be seen that the microseparation apparatus is capable of being used instead of the centrifuge to perform cytotoxicity analysis.

<Experimental Example 2>

Comparison of Microparticle Separation Efficiencies of the Apparatus for Separating the Microparticles According to the Example of the Present Invention and the Apparatus for Separating the Microparticles According to the Comparative Example The microparticle separation efficiencies of the apparatus for separating the microparticles according to Example 1 and the apparatus for separating the microparticles according to the Comparative Example were compared with each other.

FIG. 8(a) shows fluorescent microscopic pictures showing the array of the microparticles using the apparatus for separating the microparticles of Example 1 of the present invention and Comparative Example 1, and FIG. 8(b) shows the fluorescence profiles of the array.

The 6.1 μm fluorescent polystyrene microparticles (Invitrogen Corp., Carlsbad, Calif.) were suspended at a particle concentration of 10 to 3×10$^5$ in a 0.1% twin solution (Sigma-Aldrich Corp., St. Louis, Mo.) to perform the experiments. Position measurement was performed in a discharge region having a width of 500 μm. An average standard deviation (a) of two equilibrium positions was calculated to quantify the particle array (focusing) efficiency.

Figure 8:
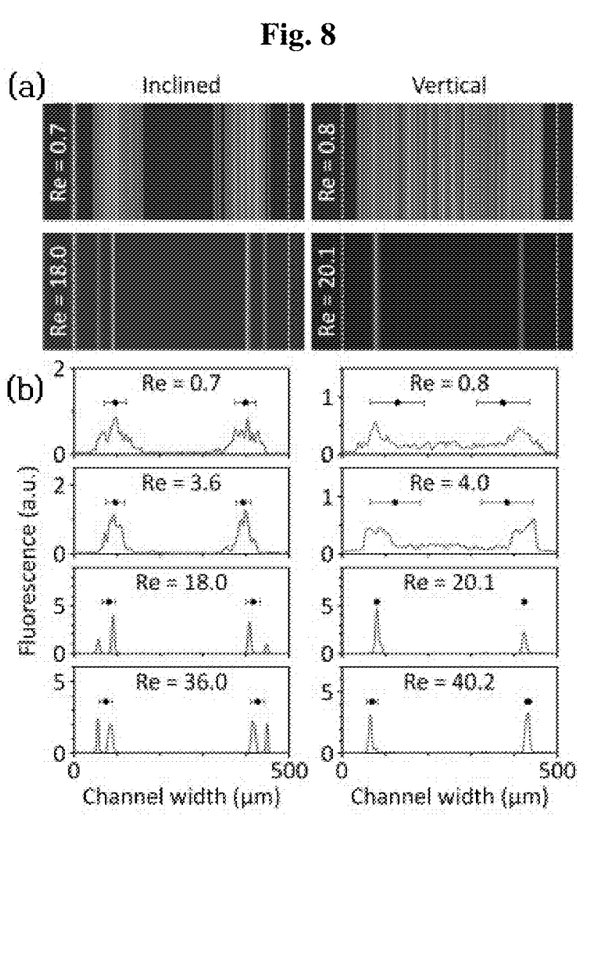

As shown in FIG. 8, when the fluid including the 6.1 μm fluorescent polystyrene microparticles and the apparatus for separating the microparticles according to the Example of the present invention were used, the average standard deviation (σ) of the two equilibrium positions was 24.8, 19.8, 16.4, and 15.1 μm when Re was 0.7, 3.6, 18.0, and 36.0, respectively.

Further, as shown in FIG. 8, when the fluid including the 6.1 μm fluorescent polystyrene microparticles and the apparatus for separating the microparticles according to Comparative Example 1 were used, the average standard deviation (σ) of the two equilibrium positions was 61.5, 59.4, 4.7, and 10.5 μm when Re was 0.8, 4.0, 20.1, and 40.2, respectively.

In the case of the apparatus for separating the microparticles according to Comparative Example 1, it could be confirmed that the average standard deviation (σ) of the two equilibrium positions was largely influenced by the flow rate and that the average standard deviation (σ) was too large to effectively separate the microparticles when Re was particularly low (10 or less). On the other hand, in the case of the apparatus for separating the microparticles according to the Example of the present invention, since the influence of Re was insignificant and the variation scope of the average standard deviation (σ) was not large, it could be confirmed that the microparticles were separated without significant influence by the flow rate.

<Experimental Example 3>

Comparison of Microparticle Separation Efficiencies of the Apparatus for Separating the Microparticles According to the Example of the Present Invention with Respect to Different Particle Sizes The 4.1 μm and 9.9 μm fluorescent polystyrene microparticles (Invitrogen Corp., Carlsbad, Calif.) were suspended at a particle concentration of $10^5$ to $3\times10^5$ in a 0.1% twin solution (Sigma-Aldrich Corp., St. Louis, Mo.) to perform the experiments. Position measurement was performed in a discharge region having a width of 500 μm. An average standard deviation (σ) of two equilibrium positions was calculated to quantify a particle array (focusing) efficiency.

Figure 9:
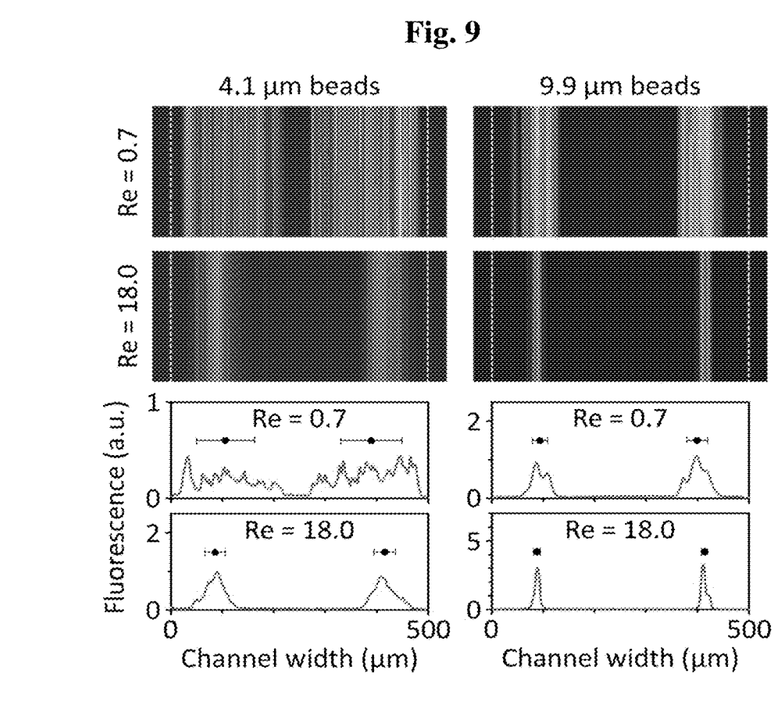
FIG. 9 shows the separation efficiency of (a) 4.1 μm-sized fluorescent polystyrene microparticles and (b) 9.9 μm-sized fluorescent polystyrene microparticles separated using the apparatus for separating the microparticles of Example 1 of the present invention.

As shown in FIG. 9, when the fluid including the 4.1 μm fluorescent polystyrene microparticles and the apparatus for separating the microparticles according to the Example of the present invention were used, the average standard deviation (σ) of the two equilibrium positions was 57.7 and 20.4 μm when Re was 0.7 and 18.0, respectively.

As shown in FIG. 9, when the fluid including the 9.9 μm fluorescent polystyrene microparticles and the apparatus for separating the microparticles according to the Example of the present invention were used, the average standard deviation (σ) of the two equilibrium positions was 17.8 and 6.5 μm when Re was 0.7 and 18.0, respectively.

From Experimental Example 3, it could be confirmed that as the particle size was increased, the average standard deviation (σ) of the two equilibrium positions was reduced, indicating that the microparticles were effectively separated.

INDUSTRIAL APPLICABILITY

According to the present invention, a cell removal process, which must be performed for the purpose of molecular analysis of a cell suspension, may be embodied in a single chip to simplify and quicken pre-treatment of samples without a high-priced large apparatus such as a centrifuge, thereby stably and precisely performing the molecular analysis.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An apparatus for separating microparticles, the apparatus comprising:
   a microfluid injection unit having an inlet opening for injecting a fluid containing the microparticles;
   a microparticle separation unit connected to the microfluid injection unit to separate the microparticles from the injected fluid;
   a first discharge unit having a first outlet opening connected to the microparticle separation unit to discharge the separated microparticles; and
   a second discharge unit having a second outlet opening connected to the microparticle separation unit to discharge the fluid from which the microparticles are removed,
   wherein the microparticle separation unit includes at least one microfluid channel unit including a primary flow channel having a primary flow direction entering from the inlet opening to the second outlet opening,
   the at least one microfluid channel unit includes expanding channel units and reducing channel units that alternately repeat,
   a lateral surface of only the reducing channel units of the at least one microfluid channel unit is vertically inclined at a predetermined angle with respect to the primary flow direction of the primary flow channel, and
   the microparticle separation unit is driven using a pressure generated by a pressure generator fastened to the microfluid injection unit;
   wherein the predetermined angle is more than 0° and less than 180° but is not 90°, with respect to primary flow direction of the primary flow channel.

2. The apparatus of claim 1, wherein the pressure generator is any one of a pipette and a syringe.

3. The apparatus of claim 1, wherein a width of the expanding channel unit is more than twice as great as a width of the reducing channel unit.

4. The apparatus of claim 1, wherein a width of the reducing channel unit is equal to or greater than a diameter of the microparticles to be separated and is up to four times as great as the diameter of the microparticles to be separated.

5. The apparatus of claim 1, wherein a height of the at least one microfluid channel unit is at least three times as great as a width of the reducing channel unit.

6. The apparatus of claim 1, wherein the expanding channel unit and the reducing channel unit are 10 μm or more in length.

* * * * *